United States Patent [19]

Mattes

[11] Patent Number: 4,859,449
[45] Date of Patent: Aug. 22, 1989

[54] MODIFIED ANTIBODIES FOR ENHANCED HEPATOCYTE CLEARANCE

[75] Inventor: Michael J. Mattes, Berkeley Heights, N.J.

[73] Assignee: Center for Molecular Medicine and Immunology, Newark, N.J.

[21] Appl. No.: 96,615

[22] Filed: Sep. 14, 1987

[51] Int. Cl.⁴ .............................................. A61K 49/00
[52] U.S. Cl. ........................................ 424/9; 128/653; 128/654; 136/173; 136/806; 530/387; 530/388; 530/389; 530/395; 530/396; 530/402
[58] Field of Search ................... 424/9; 128/553, 654; 436/173, 806; 530/396, 395, 402, 387, 388, 389

[56] References Cited

U.S. PATENT DOCUMENTS 4,624,846 11/1986 Goldenberg ............................ 424/9

OTHER PUBLICATIONS

Perry et al. Biological Abstracts, vol. 77, 1984 #84414.
Winkelhake et al, J. Biol. Chem. 251(4), 1074–1080, 1976.

*Primary Examiner*—Robert J. Warden
*Assistant Examiner*—Robert Benson
*Attorney, Agent, or Firm*—Bernhard D. Saxe

[57] ABSTRACT

Antibodies and antibody conjugates which have been modified by conjugation to, or exposure thereon, of glycoside residues that bind to the human hepatic asialoglycoprotein receptor clear rapidly from the circulation. Use of such modified antibodies and antibody conjugates for imaging and therapy of tumors and infectious lesions is advantageous when the antibodies are administered by a regional route, or when intravenous administration is accompanied by injection of a competitive hepatic lectin binding inhibitor to control the rate of clearance and optimize uptake by the target tissues.

43 Claims, No Drawings

MODIFIED ANTIBODIES FOR ENHANCED HEPATOCYTE CLEARANCE

BACKGROUND OF THE INVENTION

The present invention relates to modified antibodies bearing glycoside residues that bind to human hepatic asialoglycoprotein receptor, and their use in a method to control the rate of blood clearance of antibodies, which also may be conjugated to therapeutic and/or diagnostic agents.

Antibodies have been used as targeting vehicles for diagnostic and therapeutic agents, e.g. radioisotopes, magnetic resonance imaging (MRI) agents, toxins and cytotoxic drugs, especially in the diagnosis and treatment of cancer and certain infectious diseases. It is often useful to introduce an antibody conjugate, bearing the diagnostic or therapeutic agent, by intravenous injection, but there are instances where such a mode of administration is disadvantageous or where another mode of administration offers particular benefits.

Antibodies alone have also been shown a trigger to cytotoxic effect on cells bearing antigens to which the antibodies bind specifically. This is due to at least two distinct but probably complementary mechanisms, both of which stem from the natural effector functions of antibodies. A first mechanism has been called antibody-dependent cell-mediated cytotoxicity (ADCC), while the other has been called complement-mediated cyctoxicity. Both can be used, either alone or as part of a multi-modal treatment protocol, for therapy of tumors and infectious lesions.

Non-systemic, regional modes of administration of antibodies and antibody conjugates are especially useful in the diagnosis and treatment of tumors and infectious lesions confined within a specific body cavity, e.g., the peritoneal cavity. Intracavitary administration also can obviate the need for a tumor-specific antibody, if the targeting antibody does not bind appreciably to other tissues within the cavity where it is injected prior to passage into the bloodstream. Nevertheless, eventual migration of the antibody conjugate into the bloodstream can result in uptake by normal tissues and can also cause significant damage to bone marrow, in the case of a radiolabeled conjugate. A further problem resulting from uptake into the general circulation is an increase in background radiation, again in the case of a radiolabeled conjugate, due to blood peel activity. The efficacy and safety of certain diagnostic and therapeutic methods using non-systemically administered antibody and antibody fragment conjugates could be enhanced if a method were available for accelerating the rate of rapid clearance of the conjugate once it migrates into the bloodstream.

Conversely, the efficacy of other diagnostic and therapeutic methods using systemically administered antibodies, antibody fragments, or antibody and antibody fragment conjugates could be enhanced if it were possible to manipulate the blood clearance rate of such agents such that little or no clearance occurs for a certain time period, to allow miximum uptake of the agent by the target tissue, followed by rapid clearance of residual circulating agent.

The methods and compositions of the present invention are directed to solving these problems.

OBJECTS OF THE INVENTION

One object of the present invention is to provide an improved method of diagnosis and therapy of tumors and infectious lesions which are responsive to regionally administered antibodies and/or antibody conjugates, wherein clearance of a non-systemically administered antibody or antibody conjugate is accelerated once it is present in the general circulation.

Another object of the invention is to provide an improved method of diagnosis and therapy using modified antibodies or antibody conjugates which are injected systemically, wherein hepatocyte clearance of the conjugate is inhibited for a time, to improve the diagnostic or therapeutic effect, after which rapid clearance is effected to reduce side effects or to decrease background and enhance diagnostic resolution.

A further object of the invention is to provide reagents and kits for use in the foregoing methods.

Upon further study of the specification and appended claims, further objects and advantages of this invention will become apparent to those skilled in the art.

SUMMARY OF THE INVENTION

These objects can be achieved, in a method of treating a human patient having a tumor or infectious lesion, comprising parenterally, but non-systemically, injecting into the patient a diagnostically or therapeutically effective amount of an antibody or antibody fragment, which may also be conjugated to a radioisotope, magnetic resonance image enhancing agent, toxin or drug, wherein the antibody or antibody fragment specifically binds to a marker produced by or associated with the tumor or infectious lesion; and either taking a diagnostic image of the tumor or lesion or achieving a therapeutic result, by providing the improvement wherein the antibody is further conjugated to, or has exposed thereon, a plurality of terminal glycoside residues which bind to the human hepatocyte asialoglycoprotein receptor.

Additionally, in a method of treating a human patient having a tumor or pathological lesion, comprising injecting into the patient intravenously a diagnostically or therapeutically effective amount of an antibody or antibody fragment, conjugated to a radioisotope, magnetic resonance image enhancing agent, toxin or drug, wherein the antibody or antibody fragment conjugate specifically binds to a marker produced by or associated with the tumor or lesion; and either taking a diagnostic image of the tumor or lesion or achieving a therapeutic result, the invention provides an improvement wherein the antibody is further conjugated to, or has exposed thereon, a plurality of terminal glycoside residues which bind to the human hepatocyte asialoglycoprotein receptor; and wherein the method further comprises injecting into the patient intravenously, at, prior to or subsequent to the injection of the modified antibody or antibody fragment conjugate, an amount of a competitive inhibitor of binding to the human hepatocyte asialoglycoprotein receptor sufficient to inhibit or significantly retard hepatocyte clearance of circulating modified conjugate, for a time sufficient to permit uptake of the modified conjugate by the tumor or lesion, or to maintain the diagnostic or therapeutic effect thereof, after which time the modified conjugate is cleared from the circulation.

The invention further provides a modified antibody, comprising an antibody or antibody fragment which specifically binds a marker which is produced by or assicated with a tumor or infectious lesion, wherein the antibody or antibody fragment may also be conjugated to a radioantibody, a magnetic resonance image enhancing agent, a toxin or a drug, the antibody or antibody fragment being further conjugated to, or having exposed thereon, a plurality of terminal glycoside residues which bind to the human hepatocyte asialoglycoprotein receptor.

Sterile injectable preparations and kits containing the foregoing modified antibody are also provided, for use in the methods of the invention.

DETAILED DISCUSSION

Immunotherapy is an attractive method of treatment for certain types of tumors and infectious lesions. Antibodies or antibody fragments which bind to markers produced by or associated with such tumors or lesions, to which are conjugated therapeutically effective radioisotopes, drugs or toxins, can be used to target the therapeutic principle to the tumor or lesion site. In addition, unconjugated antibody may be an appropriate therapeutic agent, through the ADCC and/or complement-mediated cytotoxicity mechanisms, as described by Herlyn et al., Cell Immunol, 92:105, 1985. A major obstacle to using such immunotherapy has been the difficulty of obtaining antibodies which bind highly specifically to tumor or lesion antigens and do not cross-react with normal tissues.

Certain tumors and lesions are often confined to particular body cavities or regions, and regional administration of radiotherapeutic or chemotherapeutic agents has been attempted, to reduce side effects. Regional administration is used herein to connote introduction into a specific body cavity, the intracavitary route, or introduction into a non-venous circulatory system that supplies a limited region of the body such as an organ, a limb, a gland or the like. Intracavitary administration includes, e.g., intraperitoneal, intrapleural, intrathecal, and like routes. Non-venous regional circulatory administration includes intraarterial routes, e.g., injection into renal, hepatic, carotid, portal and other arteries supplying an organ or a limb, and intralymphatic routes, e.g., injection into tissue regions drained by infected or tumor-bearing lymph nodes. Intraarterial and intralymphatic administration may be effected with concomitant clamping or impedance of flow of blood or lymph out of the region of interest, to retard passage of the injected conjugate into the general circulation.

Tumors or infectious lesions that are confined to particular body cavities, or to limited regions supplied by distinct arterial blood or lymph vessels, would be candidates for the regional therapy methodology of the invention. For example, ovarian cancer is generally confined to the peritoneal cavity, even when metastasized, although extra-abdominal metastases can occur. Ovarian carcinoma is not treated effectively by current methods and is the leading cause of death among patients in the United States with gynecological malignancies. Intraperitoneal chemotherapy and radiotherapy with radiocolloids have not been dramatically successful in treating ovarian cancer, but an appropriate immunotherapy might be significantly better.

Examples of other tumors that frequently develop malignant effusions, and which therefore may be similarly treated, include colon carcinoma, lung carcinoma and mesothelioma.

Tumors and lesions confined to the brain or spinal column may be treated by intrathecal administration. Tumors and lesions in other confined, fluid-filled spaces, e.g., synovial or intraoccular fluid, may also be similarly treated.

Lymph node tumors and/or infectious lesions may be treated by intra-tissue injection of regions drained by those lymph nodes.

Organo or body regions supplied by a distinct arterial supply, and to which a tumor or infectious lesion is confined, may be treated by intraarterial injection, e.g., the liver or a single limb.

Use of intracavitary or other regional routes for administration of therapeutic antibodies and antibody conjugates can obviate the need for antibodies that are highly tumor or lesion specific. It will suffice for the antibody to specifically bind to a marker produced by or associated with the tumor or lesion and not to other types of cells or tissues to which the antibody is exposed in the particular type of regional mode of administration used.

Unless otherwise specified, the term "antibody" is used herein to include both whole immunoglobulins and antibody fragments. It will be convenient at times to use the abbreviation "antibody/fragment" to denote antibody and/or antibody fragment. Thus, the antibody may be whole IgG, IgA, IgD, IgE, IgM or a fragment such as, e.g., $F(ab')_2$, $F(ab)_2$, Fab', Fab, monovalent light/heavy chain or the like, including isotypes and subtypes thereof. It can be a polyclonal antibody, preferably an affinity-purified antibody from a human or an appropriate animal, e.g., a goat, rabbit, mouse or the like, or a monoclonal antibody prepared by conventional techniques, e.g., a murine antibody derived from a hybridoma produced by fusion of lymph or spleen cells from a mouse immunized against a tumor or infectious lesion antigen with myeloma cells from an appropriate immortal cell line.

It will be appreciated that any other type of antibody/fragment, whether produced by currently known methodology, including chimeric antibodies, hybrid antibodies, polyomas and like immunological techniques, or by recombinant DNA-mediated synthesis and expression, cassettemodification, or like techniques, can be used in the method of the present invention so long as it can function as a targeting vehicle for a diagnostic or therapeutic principle.

Examples of antibodies and antibody fragments which specifically bind markers produced by or associated with tumors or infectious lesions have been disclosed, inter alia, in Hansen et al., U.S. Pat. Nos. 3,927,193 and Goldenberg, U.S. Pat. Nos. 4,331,647, 4,348,376, 4,361,544, 4,468,457, 4,444,744, 4,460,459, 4,460,561 and 4,624,846, the disclosures of all of which are incorporated herein in their entireties by reference. These patents also disclose numerous antibodies and antibody fragments that bind to tumor markers and markers associated with infectious lesions. Methods for radiolabeling such antibodies and antibody fragments are also disclosed in the foregoing references, as are methods for conjugating such antibodies and fragments to magnetic resonance image enhancing agents.

Antibodies appropriate for i.p. therapy or imaging of ovarian carcinoma should react with the surface of ovarian carcinoma cells but not with mesothelial cells. Suitable such antibodies are known in the art, and have been disclosed by, e.g., Mattes et al., Proc. Natl. Acad. Sci. U.S.A., 81:568–572, 1984; Kabawat et al., Am. J. Clin. Pathol., 79:98–104, 1983; Tsuji et al., Cancer Res., 45:2358–2362, 1985; and Miotti et al., Intl. J. Cancer, 39:297–303, 1987.

Tumor therapy with unconjugated antibodies, making use of the natural effector functions ADCC or complement-mediated lysis, has been described by several investigators, e.g., Herlyn et al., J. Immunol., 134:1300, 1985; and Ceriani et al., Cancer Res., 47:532–540, 1987.

Tumor radioimmunotherapy is well known in the art, and has has been disclosed by, e.g., Goldenberg et al., Cancer Res., 41:4354, 1981; Jones et al., Intl. J. Cancer, 35:715–720, 1985; and Zalcberg et al., J. Natl. Cancer Inst. 72-697–702, 1984.

Therapeutically effective radioisotopes include strong beta emitters and alpha emitters, e.g., I-131, Y-90, Cu-67, Re-186, Bi-212, and the like. Such radioisotopes can be conjugated to antibodies by a variety of conventional methods. Radioiodination methods include, e.g., chloramine-T conjugation and enzymatic coupling. Radiometals can be conjugated using various conventional chelators, e.g., ethylenediaminetetraacetic acid (EDTA) and ethylenetriaminepentaacetic acid (DTPA), bis-thiosemicarbazones (TSC), porphyrins, and the like, as disclosed, e.g., by the Goldenberg patents mentioned above and by a variety of current texts. It will be appreciated that the methods and compositions of the invention are not limited by particular chelators, radioisotopes or methods of labeling.

Antitumor chemotherapeutic agents include drugs and toxins. Examples of antitumor drugs include, e.g., methotrexate (MTX), 5-fluorouracil (5-FU), cis-platinum compounds, and the like, as well as ricin A-chain and like plant toxins. Again, the invention is not limited by the particular drug or toxin conjugate.

Conjugation of such drugs to antibodies can be effected by a variety of conventional means. Coupling can be effected by a carboxyl or amine group on the drug with an amine or carboxyl group on pendant lysine or aspartate/glutamate residues on the antibody, using coupling agents such as carbodiimides, to form amide linkages. Other modes of coupling include Schiff base formation, bifunctional linker coupling between amines, or any of a multitude of other well known techniques.

The drugs can be loaded onto carrier molecules which, in turn, are coupled to the antibody, as disclosed, e.g., in Rowland, U.S. Pat. No. 4,046,722.

Therapeutic agents for treatment of infectious lesions include, e.g., radioisotopes and antibiotics. These agents can also be conjugated to antibodies by the general conventional methods used for drug and toxin conjugation.

Applying these antibody conjugates to therapy, according to the method of the present invention, involves selection of antibodies for tumor or lesion targeting that have the proper specificity for the tumor or lesion and which are not substantially cross-reactive with tissues found in the inner surfaces of the cavity or vessel into which the conjugate is injected.

For example antibodies injected intraperitoneally (i.p.) into patients with ovarian carcinoma are initially exposed to only one type of normal cell, mesothelial cells, which line all surfaces of the peritoneal cavity. Antibodies are known that bind to the surface of fresh ovarian tumor cells but not to mesothelial cells, although they do bind to certain normal epithelial cells, as noted above.

Use of such antibodies, or fragments thereof, either alone or conjugated to radioisotopes, drugs or toxins, could be effective for therapy of ovarian cancer, but the conjugates cause unwanted side effects when they migrate out of the peritoneal cavity into the bloodstream. Such migration or efflux occurs mainly through very permeable mesothelium and lymphatics on the lower surface of the diaphragm, as described by French et al., Quart. J. Exper. Physiol., 45:88–103, 1960, and this reduces the advantage of i.p. therapy. Once the conjugates reach the bloodstream, it is desirable to clear them rapidly to prevent binding to antigen-positive cells or tissues outside the peritoneal cavity.

In the case of radioisotope conjugates, rapid clearance minimizes bone marrow toxicity. Drug and toxin conjugates should be cleared rapidly to reduce toxicity to healthy tissues and organs. Rapid clearance of certain plant toxins or of particularly cytotoxic drugs may overburden the liver and would not be advantageous, but this can be determined by preliminary trials and, to some extent, mitigated by lower loading with the terminal glycoside residues that accelerate clearance of antibody conjugates containing them.

According to the invention, accelerated clearance of antibodies and antibody conjugates is achieved by conjugating them to glycosides that bind to the hepatic lectin, or by exposing such glycosides as terminal residues on existing, complex carbohydrates on the antibody. The terms "hepatic lectin", "Hepatic asialoglycoprotein receptor" or "glycoside receptor of human hepatocytes", as used herein, all mean the specific glycoprotein receptor or hepatocytes which binds certain terminal glycosides and initiates clearance of molecules bearing such terminal glycoside residues from the circulation. The properties of the receptor were reviewed by Ashwell et al., Adv. Enzymol., 41:99–128, 1974. The function of the hepatic asialoglycoprotein receptor has been extensively investigated on a molecular level, as illustrated by a recent study by Neutra et al., J. Histochem. Cytochem., 33:1134–1144, 1985.

Typically, the hepatic lectin tightly binds galactose, glucose and N-acetylgalactosamine residues, generally, D-galactosides and D-glucosides, normally in the β-glycopyranoside form, although certain α-glycosides are known to bind to the lectin. Other glycosides may be found that bind with comparable affinity, and these will also be suitable for use in the methods and compositions of the invention. The glycoside residue should be a terminal residue in order to bind to the lectin.

The glycosides can be exposed on the surface of an antibody by suitable treatment. Antibodies are glycoproteins, with carbohydrate regions containing complex, asparagine-linked carbohydrates. These complex carbohydrates will be made up of several different types of sugars, and generally contain terminal sialic acid, i.e., N-acetylneuraminic acid, residues, usually attached to galactose residues. The sialic acid residues can be removed, thereby exposing the galactose residues, using enzymes called neuraminidases, several of which are commercially available.

Desialylation procedures are well known to the ordinary skilled artisan, e.g., those reported by Ashwell, loc. cit. When neuraminidase treatment exposes sufficient numbers of galactose residues or other lectin-binding residues, it is a convenient method of modifying an antibody to accelerate its clearance from the general circulation.

However, neuraminidase-mediated desialylation does not always result in sufficient exposure of lectin-binding glycoside residues on an antibody. Moreover, antibody fragments such as Fab and F(ab')$_2$ do not normally have the complex carbohydrate region since it is removed as part of the Fc portion after enzymatic cleavage. Another alternative is to conjugate glycoside residues to the antibody or antibody fragment by any of a variety of known methods.

Lee et al., Biochem., 15:3956-3962,1976; and Krantz et al., Biochem. 15:3963-3968, 1976, disclose several methods of attaching glycosides to proteins, as well as other methods which are well known in the art for preparing such conjugates. One method uses diazonium salts of p-aminophenyl glycosides, which react with tyrosine, histidine, tryptophan and phenylalanine residues. The p-aminophenyl glycosides are commercially available, and are also readily accessible synthetically.

The p-aminophenyl glycosides can be converted to isothiocyanates by reaction with thiophosgene, and these react with lysyl residues. They can also be reacted directly with protein carboxyls, e.g., on aspartate or glutamate residues, using conventional condensing agents, e.g., dicyclohexylcarbodiimide (DCC) or 1-ethyl-3-(3-dimethylaminopropyl)carbodiimide (EDAC).

A preferred method for preparing glycosylated antibodies is amidination, especially of sugars in the form of thioglycosylamidino derivatives. The foregoing references also demonstrate that the ordinary skilled artisan in this area is aware that thioglycosylamidino derivatives of proteins can be efficiently prepared by reacting them with 2-imino-2-methoxyethyl 1-thioglycosides (IME-thioglycosides). The IME-thioglycosides are themselves conveniently prepared from cyanomethyl thioglycoside precursors, e.g., by reaction with methanolic sodium methoxide.

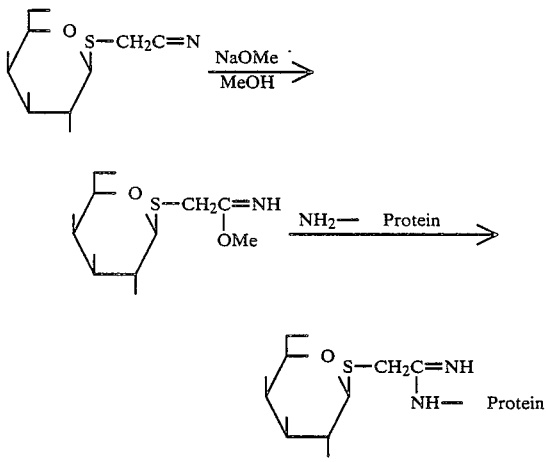

The synthesis of cyanomethyl thioglycosides was described by Lee et al., above, and such derivatives of several sugars, including D-galactose and D-glucose are commercially available. Other suitable glycosides and methods of preparation are well known in the art, as mentioned, inter alia, in the foregoing references.

The advantage of using amidination to introduce glycoside resides onto antibody conjugates is that the resultant imidates retain the charge of the lysyl residues, and the glycosylated antibodies generally retain their immunoreactivity, even at high loading, as long as critical lysine residues at the binding sites are not appreciably reacted. In contrast, diazo coupling amidation and thiourea formation can cause significant variation in charge on the protein and/or introduce hydrophobic interactions (from the phenyl groups of these derivatives). This in turn can induce conformational changes that interfere with the antibody binding function and/or biodistribution. The ease and effectiveness of this method of glycosylation appear to make it the method of choice for activating antibodies and antibody fragments towards binding by the hepatic lectin so as to accelerate their clearance from the bloodstream.

A balance must be struck between the advantage of high glycoside loading for rapid blood clearance and retention of immunoreactivity, especially if other moieties are also conjugated to the antibody, such as drugs or chelators. Radioiodination does not effect lysine residues, while many other conjugates use these residues as points of attachment, so radioiodination of antibody lysine glycosylimidates is particularly attractive for preparation of a radioimmunotherapy (RAIT) agent.

A further attractive feature of radioiodinated antibody therapy is that iodine radioisotopes are rapidly deiodinated in the liver and the radioisotope is rapidly excreted through the urinary bladder. Radiometals, on the other hand, are often retained by the liver or the kidneys and high concentrations of radioactivity can build up in these organs, causing unacceptable damage. Newer chelators are being developed that may obviate this potential problem, and these could permit the preparation of better RAIT agents.

A plurality of conjugated glycoside residues is desirable for effective acceleration of blood clearance. Preferably, at least about 10 glycoside residues per antibody/fragment will be sufficient for accelerated clearance, more particularly at least about 25 residues for rapid clearance, and perhaps more for still more rapid clearance, e.g., up to about 50-75 residues per antibody/fragment. Immunoreactivity of the glycosylated antibody conjugate can be determined using a conventional, e.g., immunoperoxidase, assay and an appropriate cell line to which the antibody binds specifically.

Generally, glycosylation will be effected to an extent which does not significantly reduce immunoreactivity, but which maximizes the clearance rate. In certain cases, especially where toxin or cytotoxic drug conjugates are used, it may be prudent to reduce the extent of glycosylation so as not to overload the liver, and cause unacceptable damage to liver function. It will be understood that some liver damage may be an acceptable price to pay for tumoricidal efficacy in patients whose cancers are otherwise refractory to chemotherapy and/or radiotherapy.

Administration of the modified antibody or antibody conjugate in a therapy protocol will be effected according to the clinical indications for the particular case. Known regional, e.g., intracavitary, antibody targeted therapy protocols will be used, e.g., those disclosed in the references mentioned above. Instead of the antibodies or antibody conjugates used therein, there will be used antibodies or radiolabeled or drugconjugated antibodies modified by exposure of, or further conjugation with, hepatic lectin-binding glycosides, according to the present invention. Because the marrow and normal organ toxicities of at least some conjugates will be reduced by rapid blood clearance, it will normally be possible to increase the dose of modified conjugate, compared to unmodified conjugate, and thus increase the therapeutic effect of each dose.

Intraperitoneal antitumor therapy is often effected following surgery, using a catheter implanted during the surgical procedure. It will be convenient to inject the therapy agent through the catheter, in a volume of solution sufficient to insure adequate contact with the interior of the cavity. It has been found that increasing the volume of injected solution can lead to longer retention and slower efflux of injected agent in the i.p. cavity.

The therapeutic efficacy of regional administration of a modified antibody conjugate according to the invention can be further enhanced, under the proper circumstances, by reducing the rate of efflux of the conjugate from the region and/or cavity into which it has been introduced into the bloodstream. This can be accomplished by any of several possible means.

Efflux of large molecules such as antibody conjugates from the peritoneal cavity normally occurs through the permeable subdiaphragmatic mesothelium into lymphatics, which in turn lead into the bloodstream. It has been found by the present inventor that ascites markedly decreases the rate of efflux of therapeutic antibody conjugates into the bloodstream. Ascites fluid accumulation is common in ovarian cancer patients, and efflux from the peritoneal cavitary is greatly delayed in such patients. Generally, such ascites accumulation occurs naturally only in patients with a large tumor burden. Even so, this will work in concert with intracavitary administration of a therapeutic antibody conjugate by reducing its rate of efflux.

In patients with a lesser tumor burden, induction of mild inflammation of the mesothelium and lymphatics, through which efflux will occur, can induce fluid accumulation and concomitant prolonged retention of the antibody conjugate in the peritoneal cavity. For example, i.p. injection of complete Freund's adjuvant, or mineral oil alone, results in mild inflammation and induces mild ascites accumulation.

Later treatment with an immunosuppressant or an anti-inflammatory drug, e.g., a corticosteroid, to counteract the effects of the inflammatory agent can be used to limit the inflammation to the period during which it aids the therapy.

Another method of reducing the rate of efflux of the antibody conjugate from the peritoneal cavity through the diaphragm is to lower the patient's breathing rate, e.g., by anesthesia, although this is only a moderately effective tactic. Clamping or otherwise blocking the lymphatics draining the diaphragm can slow drainage and efflux therethrough. Any of these methods can be applied to other regions or cavities, as will be appreciated by the ordinary skilled clinician.

The modified antibody conjugates of the invention can also be used in a systemically administered therapeutic regimen where it is desired to control the rate of blood clearance of the conjugate so that a high blood level of conjugate can be maintained for a time, during which uptake occurs by the target tissues, after which rapid clearance of circulating conjugate is effected. Prior to, together with and/or following the administration of the conjugate, a competitive inhibitor of binding to the hepatic lectin is administered to block the glycoside receptor sites of the lectin. Preferably, continuous intravenous infusion of the inhibitor is effected until such time as it is desired to initiate rapid blood pool clearance, e.g., to reduce marrow toxicity and damage to normal tissues.

An effective competitive inhibitor should be non-toxic and non-immunogenic in humans, so that relatively large amounts can be administered over a period of several days without toxicity. Suitable such inhibitors include, e.g., desialylated human serum proteins, glycoside-loaded carriers and glycosylated human serum proteins. One particularly useful asialoglycoprotein is desialylated orosomucoid ($\alpha_1$-acid glycoprotein), which is readily obtained by conventional neuraminidase treatment of orosomucoid, e.g., as described by Krantz et al., loc. cit. Desialylated fetuin is another readily available alternative. Amidination or other glycosylation of serum proteins, e.g., human serum albumin, will also produce inhibitors useful for this purpose. Amidination of an aminodextran is illustrative of a third general approach, which is to produce a glycosylated synthetic carrier molecule bearing lectin-inhibiting glycosides.

The lectin inhibitor will be administered for a time and in an amount sufficient to inhibit or retard the rate of uptake of the modified antibody or antibody conjugate by the hepatocytes and optimize its uptake by the target tissue or organ without exposing the patient to excessive risk of marrow or normal organ damage. This will vary in individual cases and the clinician must make these judgements based on intimate knowledge of the patient's history and stage of disease. The proper amount of lectin inhibitor can be ascertained by monitoring the rate of excretion of label from a glycosylated or desialylated labeled antibody or serum protein, as a function of inhibitor level.

The experiment will also show the length of time after infusion of the inhibitor is discontinued before rapid clearance of the label occurs. These parameters can be expected to vary according to the individual patient's condition and the extent to which liver and/or kidney function are impaired by disease. Design of a protocol for administration of the inhibitor, beginning either before, together with, or a period of time after the administration of the modified antibody conjugate, can be tailored to the hepatic response of the patient and the needs of the therapy modality.

It will be appreciated that the foregoing approach complements the second antibody clearance method disclosed in Goldenberg, U.S. Pat. 4,624,846, including the concept of using inhibitors of the reticuloendothelial system (RES) to avoid excessive damage to the liver. It will also be appreciated that clearance occurs by a different mechanism in the second antibody method, since it is mediated by the RES, while the present method involves hepatocyte clearance.

Methods of imaging tumors and infectious lesions, using scintigraphy or magnetic resonance, can be improved by making use of the modified antibodies and antibody conjugates according to the invention. Regional administration of a scintigraphic imaging or mri agent, in the form of an antibody conjugate, can often have advantages over systemic administration. Imaging of lymphatic structures is generally effected by administration of the imaging agent by means of a subcutaneous injection into a region which is served by a regional lymphatic drainage system and which feeds regional lymph nodes of interest. Intrathecal administration of mri agents is generally the preferred route for imaging the spinal column, and can be effective for brain imaging as well. Intracavitary administration of scintigraphic or mri agents can have the same advantages as in therapy, where the antibody is cross-reactive with tissues outside the cavity.

In all such cases, the imaging resolution and efficacy can be improved if the imaging agent is rapidly cleared from the bloodstream, once it migrates out of the region of administration and into the general circulation. Blood pool background will be reduced, and uptake by nontarget tissues will be minimized. Rapid blood clearance can reduce the time between injection and imaging and enhance the other advantages of some radioisotopes with short half-lives and mri agents with rapid rates of metabolic clearance, especially free radical agents. In addition, use of F(ab')$_2$ and especially Fab and Fab' fragment conjugates will be improved by rapid background clearance.

As for the case of therapy agents, antibodies with the proper specificities are known for many types of tumors and infectious lesions, and the same antibodies will often be used for both imaging and therapy.

Radioisotopes for radioimmunodetection (RAID) include gamma and positron emitters, with gamma energies in the range of about 50–500 KeV. Suitable such radioisotopes include, e.g., I-131, I-123, In-111, Ga-67 and Tc-99m. Labeling of antibodies with radioiodine is well known, and methods for such labeling are mentioned above. The radiometals are conjugated to antibodies by chelation or by direct labeling by a number of conventional methods. Chelators such as EDTA and DTPA have been linked to antibodies directly or through short bifunctional linkers and are used for In, Ga and Tc binding. A wide variety of other chelators have been developed and are continually being developed to more tightly bind imaging radiometals, and any one of such labeling techniques and reagents can be used in the method of the invention since it is not limited to particular imaging agents. Rather, any scintigraphic or mri antibody conjugate can be made more effective for regionally administered imaging by use of the method of the present invention because it is more efficiently cleared from general circulation and does not interfere with the imaging to the extent that would otherwise be the case.

Mri image enhancing agents for antibody-targeted imaging include a wide variety of antibody conjugates, a number of which are disclosed in Goldenberg, U.S. Pat. No. 4,624,846, or are well known in the art, as evidenced by the references cited therein. In particular, Gd(III), Mn(II), Cu(II) and other transition metal and actinide series metal ions, having several unpaired electrons in inner shells, provide the paramagnetic moments necessary for efficient enhancement of the relaxation rate of protons in their immediate vicinity. Chelation of such metal ions is effective using similar chelators to those used to bind radiometals belonging to the same transition metals and actinide metal series. Such chelators are well known to the art and their conjugation to antibodies is effected by similar conventional techniques to those used to bind chelators for radiometals, as disclosed above. Non-metallic, e.g., free radical, mri agents conjugated to antibodies will also benefit from the improved methodology of the invention for the reasons mentioned above.

The types of glycosides, methods of glycosylation and degree of loading of the glycoside residues will be similar to those use for therapeutic conjugates in most cases. Since the amounts of radioisotopes and paramagnetic metal ions will generally be low, compared to therapeutic doses, it will normally be advantageous to maximize the glycoside loading of the cojugates, consistent with retained immunoreactivity. Such loading will be substantially the same as the preferred degree of glycosylation used to potentiate rapid clearance of therapy conjugates.

Reduction in the rate of efflux from the region of administration, e.g., by inducing fluid accumulation, reduction in breathing rate, blocking flow of draining lymphatics and the like, will further enhance the uptake of imaging agent by the target tissues, and represents a preferred embodiment of the imaging method in appropriate cases. However, where target uptake is sufficiently rapid, it may be more advantageous to have relatively rapid efflux of the agent from the region and clearance from the general circulation to maximize reduction of background and improvement of imaging resolution.

Systemic, i.e., intravenous administration of scintigraphic imaging and mri agents in the form of antibody conjugates can also be improved by using the methods of the present invention. Analogously to the therapy case, it may be advantageous to manipulate the clearance rate of an antibody conjugate in the bloodstream, so that following a period of high blood concentration, to allow uptake by the target tissues, a rapid reduction in background blood pool activity can be effected. This can be achieved by using a modified, glycosylated conjugate according to the invention and injecting a competitive inhibitor of binding by the hepatic lectin. Optimization of the timing and level of administration of the inhibitor will be governed by the specific type of image being taken, the type of antibody or fragment used, the target tissue and its degree of vascular permeability and antigen concentration, among other parameters.

Again, the types of inhibitors, glycosides and antibodies, and the methods of their preparation will be closely analogous to the therapy conjugates, with the apparent differences in imaging radioisotopes or mri enhancing agents.

A sterile, injectable preparation for human therapeutic use, according to the method of the invention, will normally comprise: (a) a therapeutically effective amount of a modified antibody or antibody fragment which specifically binds a marker which is produced by or associated with a tumor or infectious lesion, the antibody or antibody fragment being conjugated to, or having exposed thereon, a plurality of terminal glycoside residues which bind to the human hepatocyte asialoglycoprotein receptor; and (b) a pharmaceutically acceptable sterile injection vehicle. Suitable such injection vehicles include, e.g., phosphate-buffered saline, optionally including human serum albumin. Where the preparation is to be used in an intravenous administration method, it will normally include a competitive hepatic lectin binding inhibitor in an amount sufficient to achieve the desired control of clearance rate. This will be the case for other injectable preparations and kits for imaging and therapy.

A sterile, injectable preparation for imaging a tumor or infectious lesion in a human patient, according to the invention, will normally comprise: (a) a diagnostically effective amount of a modified antibody or antibody fragment which specifically binds a marker which is produced by or associated with a tumor or infectious lesion, the antibody or antibody fragment being conjugated to a radioantibody or a magnetic resonance image enhancing agent, the antibody or antibody fragment being further conjugated to, or having exposed thereon, a plurality of terminal glycoside residues which bind to the human hepatocyte asialoglycoprotein receptor; and (b) a pharmaceutically acceptable sterile injection vehicle.

A kit for preparing a sterile, injectable preparation for human therapeutic use, according to the invention, will normally comprise, in one or more suitable sterile containers: (a) a therapeutically effective amount of a modified antibody or antibody fragment which specifically binds a marker which is produced by or associated with a tumor or infectious lesion, the antibody or antibody fragment being conjugated to, or having exposed thereon, a plurality of terminal glycoside residues which bind to the human hepatocyte asialoglycoprotein receptor; and (b) a pharmaceutically acceptable sterile injection vehicle.

A kit for preparing a sterile, injectable preparation for imaging a tumor or infectious lesion in a human patient, according to the invention, will normally comprise, in one or more suitable sterile containers: (a) a diagnostically effective amount of a modified antibody or antibody fragment which specifically binds a marker which is produced by or associated with a tumor or infectious lesion, the antibody or antibody fragment being conjugated to or adapted for conjugation to a radioisotope or magnetic resonance image enhancing agent, the antibody or antibody fragment being further conjugated to, or having exposed thereon, a plurality of terminal glycoside residues which bind to the human hepatocyte asialoglycoprotein receptor; and (b) a pharmaceutically acceptable sterile injection vehicle.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Therapy with radioiodinated conjugate (a) Glycosylation of MoAb

Cyanomethyl-2,3,4,6-tetra-O-acetyl-1-thio-$\beta$-D-galactopyranoside (Sigma Chemical Co.) is dissolved in methanol at 0.1M and mixed with 0.1 volume of 0.1M sodium methoxide in methanol. Aliquots are evaporated and dissolved in 0.25M sodium borate, buffer pH 8.5, containing purified anti-ovarian surface antibody IgG. After 2 hr at room temperature, the sample is dialyzed in PBS. The antibody conjugate has about 25 $\beta$-D-galactose residues thereon.

(b) Radioiodination

Radioiodination of the glycosylated antibody with I-131 is effected by substantially the same procedure as that of Example 1 of U.S. Pat. No. 4,348,376, and a sterile, pyrogen-free solution thereof is prepared substantially according to Example 5(a) of that patent.

(c) Therapy of ovarian cancer patient by i.p. administration

An ovarian cancer patient having an intraperitoneal catheter installed post-surgery, and having a number of unresectable small and medium solid tumor nodules throughout the peritoneal cavity, is injected by infusion of about 150 mCi of the solution of part (b) above, preferably diluted to a volume of about 0.5–2 liters, through the catheter. Reduction of the size of larger masses and apparent disappearance of smaller tumor foci is observed by second look surgery.

EXAMPLE 2

Intravenous therapy (a) Glycosylation of monoclonal anti-CEA-I-131

Monoclonal anti-CEA antibody is glycosylated to conjugate about 15 $\beta$-D-galactose thioglycoside residues, substantially as in Example 1(a) hereof.

(b) Radioiodination

Radioiodination and preparation of a sterile, pyrogen-free solution of the labeled conjugate are effected substantially as in Example 1(b) hereof.

(c) Therapy

Tumor therapy is effected in a patient with ovarian cancer, substantially as described in Example 7(a) of U.S. Pat. No. 4,348,376, except that a sterile solution of desialylated human $\alpha$-1 acid glycoprotein, prepared by commercially available, agarose-bound neuraminidase treatment of the commercially available protein, is fused together with the radiolabeled antibody over a period of several hours, and infusion of the inhibitor alone is continued for 36 hr, after which it is discontinued, and rapid clearance of the circulating antibody conjugate is observed. Bone marrow toxicity of the conjugate is reduced over a similar dose administered without rapid hepatocyte clearance.

EXAMPLE 3

Systemic scintigraphy with Tc-99m-Fab

Anti-CEA Fab is conjugated with 25 $\beta$-D-galactose residues and with 2–3 bis-thiosemicarbazone chelators, then labeled with Tc-99m, using stannous chloride reduction of pertechnetate. The conjugate is injected intravenously, together with a sterile solution of desialylated human $\alpha$-1 acid glycoprotein, prepared by neuraminidase treatment of the commercially available protein. Infusion of the inhibitor is discontinued after 12 hr, after which rapid clearance of the circulating Fab conjugate is observed. The rapid clearance of circulating, non-targeted Fab conjugate permits scintigraphic imaging of colorectal cancer sooner than otherwise, and with higher resolution, either with or without subtraction.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a method of treating a human patient having a tumor or infectious lesion, comprising parenterally, but non-systemically, injecting into said patient a therapeutically effective amount of an antibody or antibody fragment, conjugated to a radioisotope, toxin or drug, wherein said antibody or antibody fragment conjugate specifically binds to a marker produced by or associated with said tumor or infectious lesion, the improvement wherein said antibody or antibody fragment conjugate is modified by being further conjugated to, or having exposed thereon, a plurality of terminal glycoside residues which bind to the human hepatocyte asialoglycoprotein receptor.

2. The method of claim 1, wherein said conjugated glycoside residue is a galactose, N-acetylgalactosamine or glucose residue.

3. The method of claim 1, wherein said antibody or antibody fragment is conjugated to a radioisotope.

4. The method of claim 1, wherein said antibody or antibody fragment is conjugated to a drug or toxin.

5. The method of claim 1, wherein said antibody or antibody fragment conjugate specifically binds to a marker produced by or associated with a tumor.

6. The method of claim 5, wherein said tumor is an ovarian tumor.

7. The method of claim 1, wherein said antibody or antibody fragment conjugate specifically binds to a marker produced by or associated with an infectious lesion.

8. The method of claim 1, wherein said non-systemic parenteral injection is effected by an intraperitoneal route.

9. The method of claim 1, which further comprises reducing the rate of efflux of said conjugate into the bloodstream.

10. In a method of treating a human patient having a tumor or infectious lesion, comprising parenterally, but non-systemically, injecting into said patient a therapeutically effective amount of an antibody or antibody fragment which specifically binds to a marker produced by or associated with said tumor or infectious lesion, the improvement wherein said antibody or antibody fragment is modified by being conjugated to, or having exposed thereon, a plurality of terminal glycoside residues which bind to the human hepatocyte asialoglycoprotein receptor.

11. The method of claim 10, wherein said conjugated glycoside residue is a galactose, N-acetylgalactosamine or glucose residue.

12. The method of claim 10, wherein said antibody or antibody fragment specifically binds to a marker produced by or associated with a tumor.

13. The method of claim 12, wherein said tumor is an ovarian tumor.

14. In a method of treating a human patient having a tumor or infectious lesion, comprising injecting into said patient intravenously a therapeutically effective amount of an antibody or antibody fragment, conjugated to a radioisotope, toxin or drug, wherein said antibody or antibody fragment conjugate specifically binds to a marker produced by or associated with said tumor or infectious lesion, The improvement wherein said antibody or antibody fragment conjugate is modified by being further conjugated to, or having exposed thereon, a plurality of terminal glycoside residues which bind to the human hepatocyte asialoglycoprotein receptor; and wherein said method further comprises injecting into said patient intravenously, at, prior to or subsequent to the injection of said modified antibody or antibody fragment conjugate, an amount of a competitive inhibitor of binding to the hepatocyte asialoglycoprotein receptor sufficient to inhibit or significantly retard hepatocyte clearance of circulating modified conjugate, for a time sufficient to permit uptake of said modified conjugate by said tumor or infectious lesion, after which time said modified conjugate is cleared from the circulation.

15. In a method of imaging a human patient having a tumor or infectious lesion, comprising parenterally, but non-systemically, injecting into said patient a diagnostically effective amount of an antibody or antibody fragment, conjugated to a radioisotope or magnetic resonance image enhancing agent, wherein said antibody or antibody fragment conjugate specifically binds to a marker produced by or associated with said tumor or infectious lesion; and obtaining a scintigraphic or magnetic resonance image of said tumor or infectious lesion, the improvement wherein said antibody or antibody fragment conjugate is modified by being further conjugated to, or having exposed thereon, a plurality of terminal glycoside residues which bind to the human hepatocyte asialoglycoprotein receptor.

16. The method of claim 15, wherein said conjugated glycoside residue is a galactose, N-acetylgalactosamine or glucose residue.

17. The method of claim 15, wherein said antibody or antibody fragment is conjugated to a radioisotope, and a scintigraphic image is obtained.

18. The method of claim 15, wherein said antibody or antibody fragment is conjugated to a magnetic resonance image enhancing agent, and a magnetic resonance image is obtained.

19. The method of claim 15, wherein said antibody or antibody fragment conjugate specifically binds to a marker produced by or associated with a tumor.

20. The method of claim 19, wherein said tumor is an ovarian tumor.

21. In a method of imaging a human patient having a tumor or infectious lesion, comprising injecting into said patient intravenously a diagnostically effective amount of an antibody or antibody fragment, conjugated to a radioisotope or magnetic resonance image enhancing agent, wherein said antibody or antibody fragment conjugate specifically binds to a marker produced by or associated with said tumor or infectious lesion; and obtaining a scintigraphic or magnetic resonance image of said tumor or infectious lesion, the improvement wherein said antibody or antibody fragment conjugate is modified by being further conjugated to, or having exposed thereon, a plurality of terminated glycoside residues which bind to the human hepatocyte asialoglycoprotein receptor; and wherein said method further comprises injecting into said patient intravenously, at, prior to or subsequent to the injection of said modified antibody or antibody fragment conjugate, an amount of a competitive inhibitor of binding to the hepatocyte asialoglycoprotein receptor sufficient to inhibit or significantly retard hepatocyte clearance of circulating modified conjugate, for a time sufficient to permit uptake of said modified conjugate by said tumor or infectious lesion, after which time said modified conjugate is cleared from the circulation.

22. The method of claim 21, wherein said conjugated glycoside residue is a galactose, N-acetylgalactosamine or glucose residue.

23. The method of claim 21, wherein said antibody or antibody fragment is conjugated to a radioisotope, and a scintigraphic image is obtained.

24. The method of claim 21, wherein said antibody or antibody fragment is conjugated to a magnetic resonance image enhancing agent, and a magnetic resonance image is obtained.

25. The method of claim 21, wherein said antibody or antibody fragment conjugate specifically binds to a marker produced by or associated with a tumor.

26. A modified antibody conjugate, comprising an antibody or antibody fragment which specifically binds a marker which is produced by or associated with a tumor or infectious lesion, said antibody or antibody fragment being conjugated to a radioisotope, a magnetic resonance image enhancing agent, a toxin or a drug, said antibody or antibody fragment being further conjugated to, or having exposed thereon, a plurality of terminal glycoside residues which bind to the human hepatocyte asialoglycoprotein receptor.

27. The modified antibody conjugate of claim 26, wherein said conjugated glycoside residue is a galactose, N-acetylgalactosamine or glucose residue.

28. The modified antibody conjugate of claim 26, wherein said antibody or antibody fragment is conjugated to a radioisotope.

29. The modified antibody conjugate of claim 26, wherein said antibody or antibody fragment is conjugated to a magnetic resonance image enhancing agent.

30. The modified antibody conjugate of claim 26, wherein said antibody or antibody fragment specifically binds to a marker produced by or associated with a tumor.

31. The modified antibody conjugate of claim 30, wherein said tumor is an ovarian tumor.

32. The modified antibody conjugate of claim 26, wherein said antibody or antibody fragment conjugate specifically binds to a marker produced by or associated with an infectious lesion.

33. A sterile, injectable preparation for human therapeutic use, comprising: (a) a therapeutically effective amount of a modified antibody or antibody fragment which specifically binds a marker which is produced by or associated with a tumor or infectious lesion, said antibody or antibody fragment being conjugated to, or having exposed thereon, a plurality of terminal glycoside residues which bind to the human hepatocyte asialoglycoprotein receptor; and (b) a pharmaceutically acceptable sterile injection vehicle.

34. A sterile, injectable preparation for imaging a tumor or infectious lesion in a human patient, comprising: (a) a diagnostically effective amount of a modified antibody or antibody fragment which specifically binds a marker which is produced by or associated with a tumor or infectious lesion, said antibody or antibody fragment being conjugated to a radioisotope or a magnetic resonance image enhancing agent, said antibody or antibody fragment being further conjugated to, or having exposed thereon, a plurality of terminal glycoside residues which bind to the human hepatocyte asialoglycoprotein receptor; and (b) a pharmaceutically acceptable sterile injection vehicle.

35. A kit for preparing a sterile, injectable preparation for human therapeutic use, comprising, in one or more suitable sterile containers: (a) a therapeutically effective amount of a modified antibody or antibody fragment which specifically binds a marker which is produced by or associated with a tumor or infectious lesion, said antibody or antibody fragment being conjugated to, or having exposed thereon, a plurality of terminal glycoside residues which bind to the human hepatocyte asialoglycoprotein receptor; and (b) a pharmaceutically acceptable sterile injection vehicle.

36. The kit of claim 35, which further comprises (c) an effective inhibiting amount of a competitive inhibitor of binding to the human hepatocyte asialoglycoprotein receptor.

37. A kit for preparing a sterile, injectable preparation for imaging a tumor or infectious lesion in a human patient, comprising, in one or more suitable sterile containers: (a) a diagnostically effective amount of a modified antibody or antibody fragment which specifically binds a marker which is produced by or associated with a tumor or infectious lesion, said antibody or antibody fragment being conjugated to or adapted for conjugation to a radioisotope or magnetic resonance image enhancing agent, said antibody or antibody fragment being further conjugated to, or having exposed thereon, a plurality of terminal glycoside residues which bind to the human hepatocyte asialoglycoprotein receptor; and (b) a pharmaceutically acceptable sterile injection vehicle.

38. The kit of claim 37, which further comprises (c) an effective inhibiting amount of a competitive inhibitor of binding to the human hepatocyte asialoglycoprotein receptor.

39. The method of claim 1, wherein said glycoside residue is a galactose residue.

40. The method of claim 10, wherein said glycoside residue is a galactose residue.

41. The method of claim 15, wherein said glycoside residue is a galactose residue.

42. The method of claim 21, wherein said glycoside residue is a galactose residue.

43. The modified antibody conjugate of claim 26, wherein said glycoside residue is a galactose residue.

* * * * *